United States Patent

Cameron et al.

[11] Patent Number: 5,285,779
[45] Date of Patent: Feb. 15, 1994

[54] METHOD AND APPARATUS FOR A CARDIAC DEFIBRILLATOR HIGH VOLTAGE CHARGING CIRCUIT

[75] Inventors: David B. Cameron; Paul D. Bliley, both of McMinnville, Oreg.

[73] Assignee: Hewlett-Packard Company, Palo Alto, Calif.

[21] Appl. No.: 858,808

[22] Filed: Mar. 27, 1992

[51] Int. Cl.$^5$ ............................................. A61N 1/00
[52] U.S. Cl. ............................................. 607/5; 320/1
[58] Field of Search ................... 128/419 D, 421, 422; 307/66, 150; 315/241 P; 320/1

[56] References Cited

U.S. PATENT DOCUMENTS

| | | | |
|---|---|---|---|
| 3,624,484 | 11/1971 | Colyer | 128/422 |
| 3,654,537 | 4/1972 | Coffey | 320/1 |
| 3,704,393 | 11/1972 | Digney, Jr. et al. | 320/1 |
| 3,851,239 | 11/1974 | Suzuki | 321/11 |
| 4,068,151 | 1/1978 | Harrison | 320/1 |
| 4,077,143 | 3/1978 | Partridge | 128/419 D |
| 4,079,265 | 3/1978 | Woodburn | 320/1 |
| 4,682,082 | 7/1987 | MacAskill et al. | 315/219 |
| 4,733,153 | 3/1988 | Katzenstein | 320/1 |
| 4,736,149 | 4/1988 | van den Eijnden | 320/1 |
| 5,003,191 | 3/1991 | Boyle et al. | 307/109 |

Primary Examiner—William E. Kamm
Assistant Examiner—Marianne Parker

[57] ABSTRACT

A variable rate defibrillator charging circuit includes a power transformer that accepts an internal battery output and the output from an AC-to-DC converter on separate primary windings. The secondary winding of the transformer is coupled through a rectifier to a storage capacitor. The transformer operates in a fly-back mode whereby energy is discharged into the storage capacitor when the power supplies discontinue charging the transformer. After energy in the transformer is discharged into the storage capacitor, the power supplies are reactivated, recharging the transformer. The separate primary windings of the transformer provide a fast, reliable, low cost means for charging the storage capacitor with multiple power supplies. The AC power source feeding the AC-to-DC converter is detachable allowing the defibrillator to be operated remotely whereby the storage capacitor is charged solely from the internal battery. The charging circuit monitors the output voltage levels of both the battery and the AC-to-DC converter and enables or disables the power supplies in accordance to their ability to charge the storage capacitor within a predetermined amount of time. The energy in the storage capacitor, which is eventually discharged into a patient, is monitored to prevent overcharging.

20 Claims, 5 Drawing Sheets

METHOD AND APPARATUS FOR A CARDIAC DEFIBRILLATOR HIGH VOLTAGE CHARGING CIRCUIT

BACKGROUND OF THE INVENTION

This invention relates to cardiac defibrillators and more particularly to defibrillators powered from alternate power sources.

Cardiac defibrillators generate a high voltage output that is discharged from a capacitor into a patient to perform either defibrillation or synchronized cardioversion. The life of a patient may depend upon a defibrillator's reliability and whether it can generate sufficient energy in a limited amount of time. A defibrillator charger circuit, which operates from a single power supply, is described in Hewlett-Packard operating manual, 43100A Defibrillator/Monitor and Recorder, May 1988, Part No. 43100-91909 and is incorporated by reference.

It is desirable that the defibrillator have the capacity to operate in different situations; for example, in a hospital emergency room or in remote locations such as an ambulance. It is therefore necessary that the defibrillator's high voltage charging transformer be able to efficiency receive and transform power from DC power supplies with different output characteristics. For example, the transformer should typically be capable of receiving power from either an AC-to-DC converter (e.g. for 120 volt AC "plug in" type source) or from a DC battery.

Several problems are associated with designing a defibrillator to operate from more than one power supply. For example, power supply switching circuitry operating at high current levels reduces the reliability of the overall defibrillator system. Fault conditions on one of the power supplies may alter the normal output characteristics of the second power supply. Due to the high current from the power supply to the transformer, it is also necessary that the switching circuit have low energy loss characteristics. However, components that have high current ratings and provide low energy loss are expensive and typically require additional logic circuitry. In addition, an AC-to-DC converter is typically not capable of supplying as much peak current as a battery, so a transformer that is optimized for the battery is not optimized for the AC-to-DC converter. This difference can adversely affect the amount of time required to properly charge the defibrillator's storage capacitor.

Accordingly, a need exists for a cardiac defibrillator that is reliable, capable of producing a high voltage output in a minimal amount of time, and inexpensive while capable of being energized from multiple power supplies.

SUMMARY OF THE INVENTION

One object of the present invention is to energize a cardiac defibrillator from multiple power supplies with reliable switching between supplies.

A second object is to increase the fault tolerance of a cardiac defibrillator energized by alternate power supplies when voltage or current conditions of one of the supplies is outside normal operating ranges.

Another object is to reduce the charge time of a cardiac defibrillator by single or multiple power supplies in coordination with the power supply output conditions.

Yet another object is to reduce charge failures in cardiac defibrillators by providing automatic on-line battery recharging.

The invention is a quick-charging, high-reliability cardiac defibrillator that uses a dual primary high voltage transformer to energize a high voltage storage and discharge capacitor from at least two DC power supplies. Power is primarily supplied to the transformer by a battery supply; however, depending upon the battery output, a second DC power supply can be activated. The power supplies operate separately or together to supply energy to the transformer. The transformer operates in a fly-back mode whereby current is not allowed to pass through the secondary winding until the power supplies have deactivated. Upon deactivation of the power supplies, current begins to flow through the secondary winding, discharging the energy stored in the transformer into the high voltage storage capacitor. The energy in the storage capacitor is then discharged into a patient.

The dual primary winding high voltage transformer accepts the internal battery supply on a first primary winding and the output from an AC-to-DC converter on a secondary primary winding. Providing two primary windings allows the output characteristics for each power supply to be individually matched. Thus, the transformer allows fast, high current charging from the battery, and slower low current charging from the AC-to-DC converter. Since each power supply is separately coupled to the transformer by a primary winding, fault conditions occurring on either power supply are isolated.

The AC power source feeding the AC-to-DC converter is detachable, allowing the defibrillator to be operated remotely. With the converter detached, the storage capacitor is charged solely from the internal battery. The battery is not allowed to provide current to the transformer if the battery output voltage would drop below the level necessary to maintain normal defibrillator operation. When both the AC power source and the battery are attached to the defibrillator, additional circuitry monitors the output voltage level of both power supplies. Accordingly, if the battery has a sufficient output voltage, the output from the AC-to-DC converter is restricted in supplying energy to the transformer. When the battery has a low output voltage, however, output from the AC-to-DC power supply contributes more energy to the charging of the transformer. If the battery is severely discharged, power from the AC-to-DC converter output is used to recharge the battery.

The power supplies are activated with a pulse width modulated signal. Each modulation cycle increases the amount of energy in the stage capacitor. The number of cycles and the duration of each cycle are controlled by external defibrillator control circuitry. The time required to discharge the transformer is dependant upon the amount of energy already stored in the capacitor. Therefore, the power supplies are activated at a variable rate that depends upon the time required for energy to transfer from the transformer to the storage capacitor. The pulse width modulator is fed parametric information from monitoring circuits on both the primary and secondary sides of the transformer. The modulator in turn disables the power supplies if excessive current or voltage levels occur in the defibrillator system.

The secondary coil of the transformer is coupled by a diode to the storage capacitor. Upon activation of power on the primary side of the transformer, the diode becomes reverse biased. This prevents current from passing through the secondary winding, causing the transformer to store energy. Upon disabling the power supplies (e.g. the power supplies discontinue charging the transformer), the voltage on the secondary winding increases, forward biasing the diode. The transformer then discharges energy into the storage capacitor. The voltage across the storage capacitor is monitored and charging cycles are repeated until the storage capacitor reaches a preset voltage level.

Therefore, the dual primary, high voltage transformer and the associated charging circuitry provide a low cost, reliable means for quickly charging a cardiac defibrillator.

The foregoing and other objects, features and advantages of the invention will become more readily apparent from the following detailed description of a preferred embodiment which proceeds with reference to the accompanying drawings.

DETAILED DESCRIPTION

Description of Prior Art Defibrillator

Figure 1:
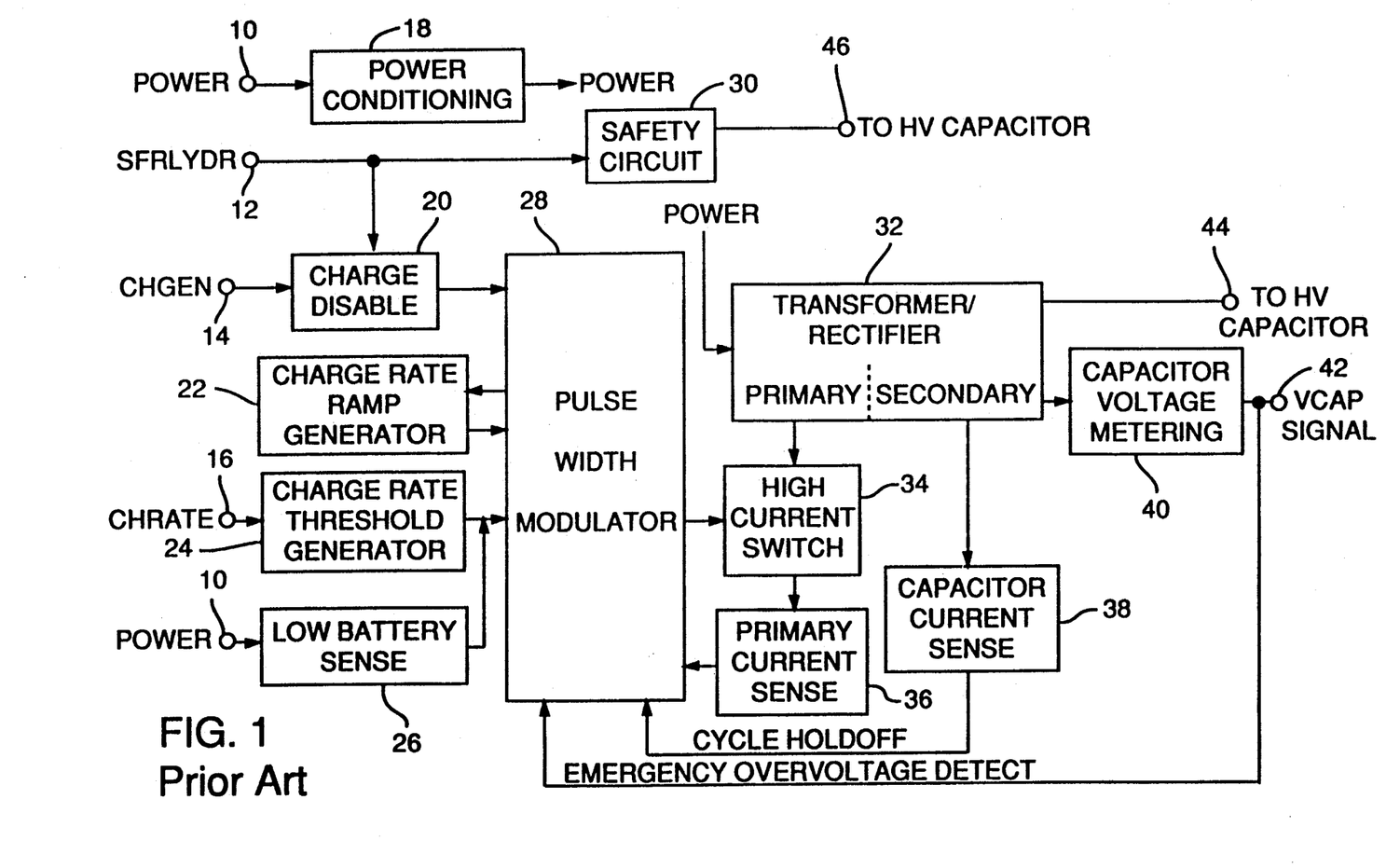
FIG. 1 is a block diagram for a prior art cardiac defibrillator charging circuit energized from a single power supply.

FIG. 1 shows the general arrangement of the charging circuit for the Hewlett-Packard 43100A Defibrillator/Monitor with Recorder mentioned above. A power conditioning circuit 18 receives a power supply input. The output of power conditioning circuit 18 is coupled to the primary winding of transformer/rectifier circuit 32. A conventional defibrillator control board (not shown) supplies control signals: safety relay drive (SFRLYDR), charge enable (CHGEN), and charge rate (CHRATE), to the defibrillator charging circuit in FIG. 1.

A safety circuit 30 is coupled across an energy storage capacitor (not shown) and receives SFRLYDR. A charge disable circuit 20 is coupled at the input to the SFRLYDR and CHGEN signals, and has an output to the shutdown pin of a pulse width modulator (PWM) 28. A charge rate ramp generator circuit 22 is driven by a voltage output from PWM 28 and has an output coupled to the oscillator/comparator input of PWM 28.

A charge rate threshold generator circuit 24 receives the CHRATE signal at its input and its output is coupled to the inverting comparator input on PWN 28. A low battery sense circuit 26 is coupled to the input from the power supply, and has an output coupled to the inverting comparator input of PWM 28.

PWM 28 is a Unitrode 3524A, pulse width modulator. The modulator receives input signals from charge disable circuit 20, charge rate ramp generator circuit 22, charge rate threshold generator circuit 24, low battery sense circuit 26, a primary current sense circuit 36, a capacitor current sense circuit 38, and a capacitor voltage metering circuit 40. The output of PWM 28 drives a high current switch 34.

Transformer/rectifier circuit 32 is coupled at a first terminal of a primary winding to the output of power conditioning circuit 18 and is coupled at a second terminal of the primary winding to high current switch 34. The output of high current switch 34 feeds primary current sense 36. The secondary winding of transformer/rectifier circuit 32 is a high voltage output coupled to an energy storage capacitor (not shown), monitoring signal outputs coupled to capacitor voltage metering circuit 40 and capacitor current sense circuit 38.

The defibrillator charger circuit in FIG. 1 is a variable frequency, fly-back DC-DC high voltage charging circuit that operates from a single power supply. A battery supplies a DC voltage to power conditioning circuit 18. If the battery produces a large current surge, power conditioning circuit 18 provides bypassing for the defibrillator charging circuit. If there is no current surge, the battery voltage is fed directly into the primary winding of transformer/rectifier circuit 32. The voltage from the battery is stepped up by the transformer and eventually discharged into the energy storage capacitor. The energy storage capacitor, when charged sufficiently, is then discharged, through additional defibrillator control circuitry (not shown), into a patient.

Figure 3:
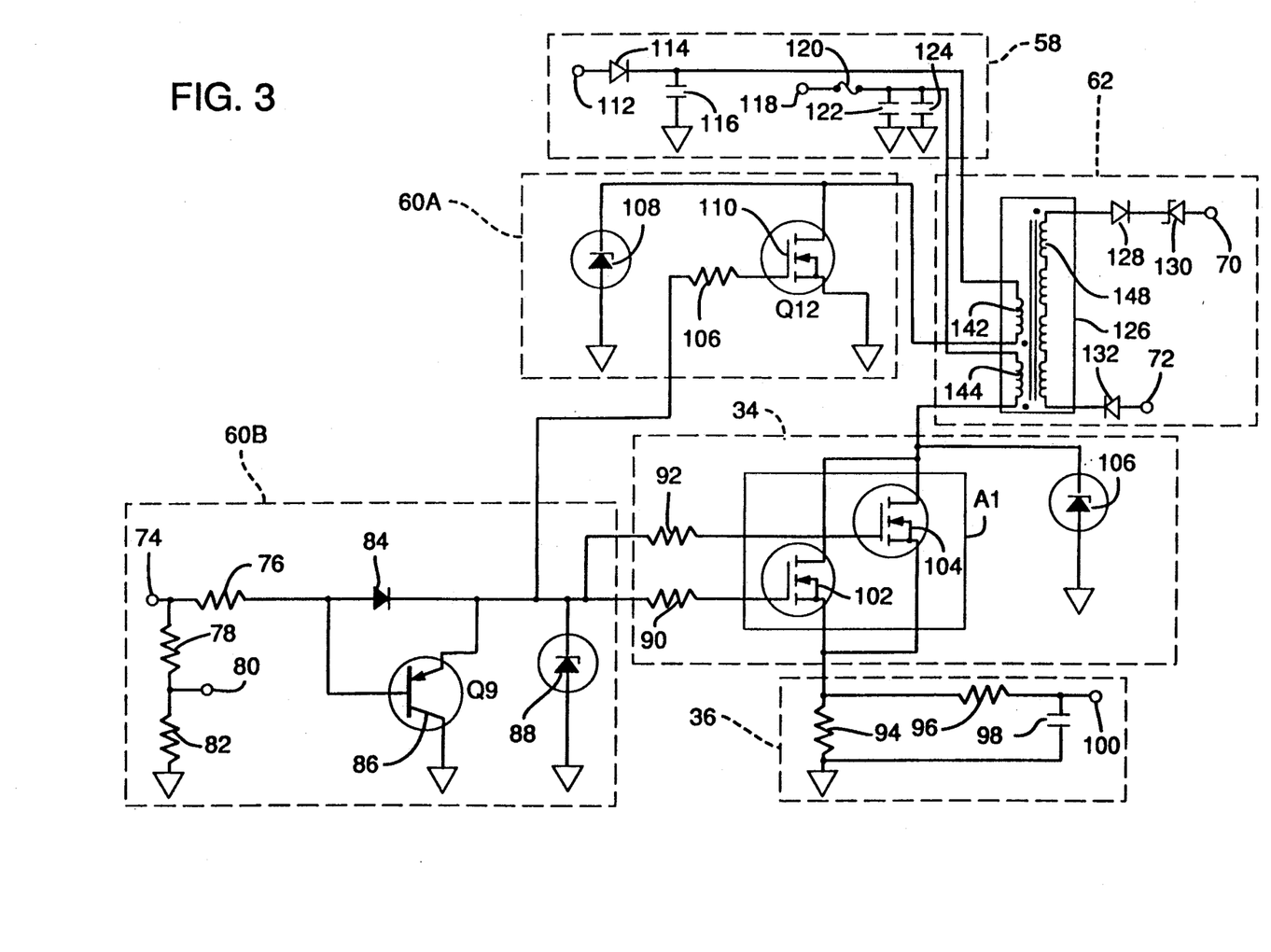
FIG. 3 is a detailed circuit diagram of the dual primary transformer/rectifier, low current switch/switch driver, high current switch, primary current sense, and power disable in FIG. 2.

The secondary winding of the transformer is coupled by a diode (inside transformer/rectifier circuit 32), to the storage capacitor (see FIG. 3). The diode causes the transformer to operate in a fly-back mode, described below in the discussion of FIG. 3. In a fly-back mode, the transformer stores energy when the battery is charging the transformer primary winding. When the battery stops charging, the transformer discharges stored energy into the storage capacitor. Then, if re-enabled, the battery recharges the transformer. This process is repeated until the storage capacitor is charged to a level set by the defibrillator control board. Safety circuit 30 provides a switchable shunt resistor for discharging the storage capacitor. The shunt resistor is typically connected across the storage capacitor when power is disconnected from the defibrillator charging circuit.

Current from the battery only flows through the primary winding of the transformer when high current switch 34 is turned on by PWM 28. The pulse width modulator, in turn, is controlled by charge disable 20, charge rate ramp generator 22, charge rate threshold generator 24, low battery sense 26, primary current sense 36, capacitor current sense 38, and capacitor voltage metering 40.

To initially enable the pulse width modulator, the external defibrillator control board drives CHGEN and SFRLYDR low. This causes charge enable 20 to generate a high impedance output, enabling the shutdown pin on PWM 28. For the output of PWN 28 to go high, its shutdown pin must be enabled and the output voltage of charge rate ramp generator 22 must be less than the voltage output of charge rate threshold generator 24.

The charge rate ramp generator 22 supplies an output voltage to PWM 28 that increases approximately linearly with time. This voltage is compared in PWM 28 with the output of charge rate threshold generator 24. As the output voltage of charge rate ramp generator 22 increases, but is still less than the charge rate threshold generator output, the output of PWM 28 goes high, turning on high current switch 34.

When the high current switch is turned on, the battery begins charging the transformer through the primary winding. To increase the amount of time PWM 28 remains on, the voltage level of CHRATE signal is increased by the defibrillator control board. The higher voltage requires more time for the output of charge rate ramp generator 22 to reach the threshold generator output voltage. Thus, PWM 28 remains active longer, allowing the power supply to provide more energy to the transformer/rectifier circuit. To reduce the amount of time PWM 28 remains on, the voltage of the CHRATE signal is reduced. This produces a lower voltage at the output of charge rate threshold genertor 24, allowing the charge rate ramp generator to reach the charge rate threshold voltage in a shorter amount of time. The battery is thereby activated for a shorter time, transferring less energy into the storage capacitor.

When the output of charge rate ramp generator 22 equals the output voltage of charge rate threshold generator 24, a voltage comparator inside PWM 28 disables the modulator output, and resets the output of charge rate ramp generator 22 to zero volts. The output of charge rate ramp generator 22 immediately begins increasing, starting another charging cycle. If no alternative inputs to PWM 28 go into a disable state, the output of PWM 32 again goes high and the transformer is again charged.

Charge rate threshold generator 24 also disables PWM 28 when the CHRATE signal is at zero volts (e.g. cable from the defibrillator control board to the defibrillator charger disconnected). If the CHRATE signal is a positive voltage, however, the output of charge rate threshold generator 24 goes into a high impedance state, removing the disable signal from PWM 28.

The charge rate ramp generator output voltage rises at a slower rate for lower battery voltage outputs. This partially compensates for otherwise slowed charging under low battery output conditions.

Capacitor current sense 38 monitors the secondary side current, keeping PWM 28 off when the transformer is discharging energy into the storage capacitor. The capacitor current sense allows the modulator to begin another charging cycle when secondary current no longer passes from the transformer to the storage capacitor. Thus, the defibrillator charging circuit operates at variable frequencies depending on the rate in which energy is transferred from the transformer to the storage capacitor.

Capacitor voltage metering circuit 40 monitors the voltage across the storage capacitor. The capacitor voltage is scaled, then fed back to PWM 28. When the storage capacitor voltage is excessive, PWM 28 is disabled to prevent any further charging of the capacitor.

The scaled storage capacitor voltage is also fed back to the defibrillator control board. The control board allows the charging circuit to continue supplying energy to the transformer (e.g. keep both CHGEN and SFRLYDR low and CHRATE high) until the storage capacitor is fully charged.

Low battery sense 26 disables PWM 28 if the battery voltage is too low and primary current sense 36 disables PWM 28 if excessive current passes through high current switch 34.

Problems with the Prior Art

The main problem with the defibrillator charging circuit in FIG. 1 is that there is only one path for supplying power to the transformer. For example, to change power sources, either the battery must be physically disconnected so the second supply can be connected, or switching circuitry must be provided that disconnects the battery and reconnects the output from a second power supply (e.g., an AC-to-DC converter) to power conditioning circuit 18. One problem with the latter approach is providing reliable switching circuitry that also provides low energy loss for the high current drawn by transformer/rectifier circuit 32. This typically requires a high current relay, or a field effect transisitor with a very low drain/source resistance. Both of these parts are expensive and require additional drive logic.

In addition, the AC-to-DC converter is not capable of supplying as much peak current as the battery, so if transformer/rectifier circuit 32 is optimized for the battery it is not optimized for the AC-to-DC converter.

Figure 2:
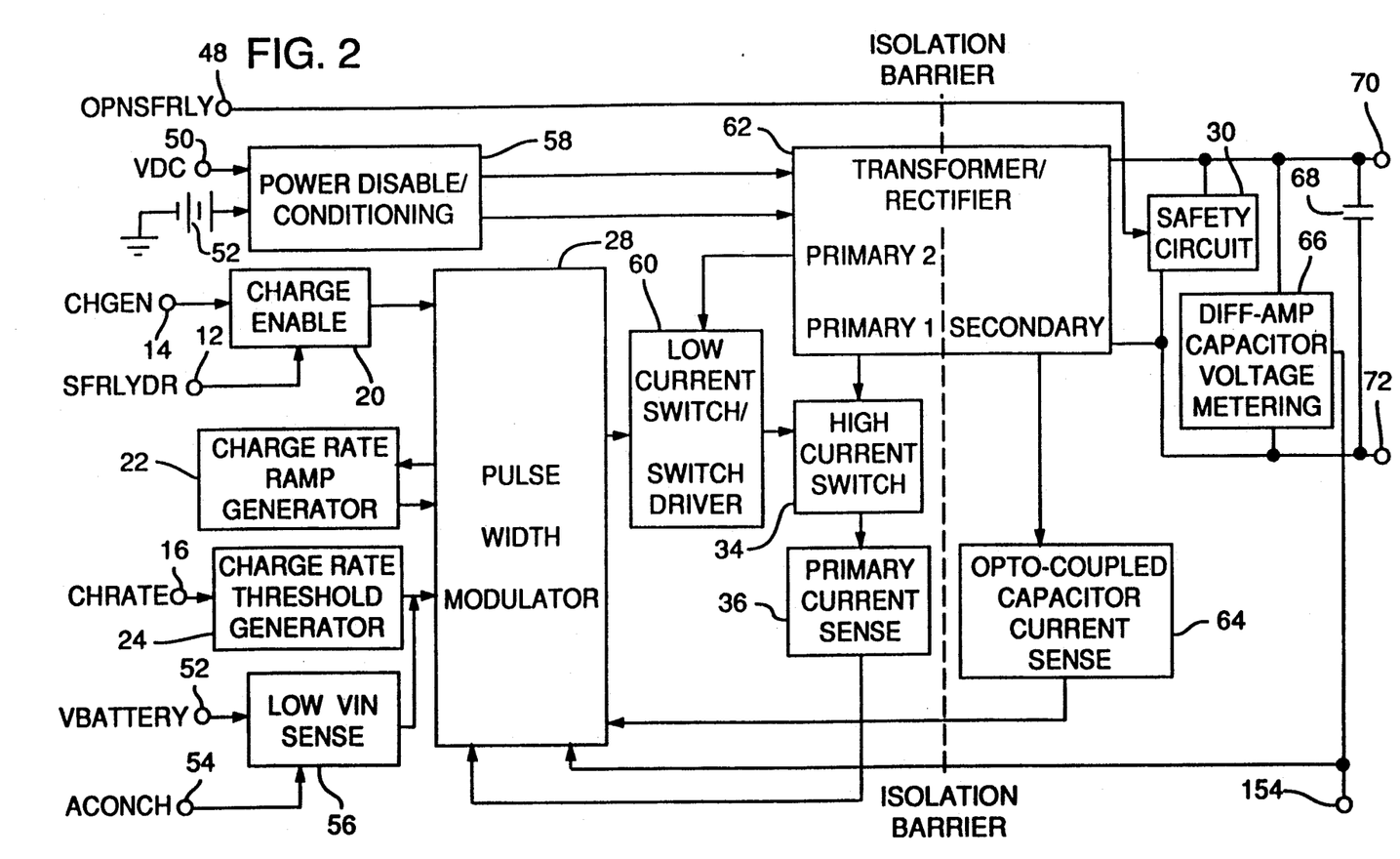
FIG. 2 is a block diagram of a cardiac defibrillator charging circuit energized from a battery and an AC/DC power supply in accordance with the invention.

This invention solves both of these problems by providing a transformer with two primary windings. By providing a dual primary transformer, each winding can be tailored to its source of current, allowing fast, high current charging from the battery, and slower, lower current charging from the AC-to-DC converter. In addition, since each source has its own primary, there is no need to switch the inputs, and the transformer will draw current from whichever source is available. The separate, dual primary transformer also isolates faults on either power supply. FIG. 2 shows the general arrangement for a preferred embodiment of a dual power supply defibrillator charging circuit in accordance with the invention.

DESCRIPTION OF THE PREFERRED EMBODIMENT

Referring to FIG. 2, charge enable 20, charge rate ramp generator 22, charge rate threshold generator 24, high current switch 34, and primary current sense 36, operate substantially the same as described in FIG. 1 and so as identified by like reference numerals. Safety circuit 30 also operates substantially the same as described in FIG. 1, only it is now driven by open safety relay signal (OPNSFRLY) from the above-described defibrillator control board (not shown). The OPNSFRLY signal is the inverted value of signal SFRLYDR.

Power disable/conditioning circuit 58 performs substantially the same circuit bypassing function as power conditioning circuit 18 in FIG. 1, but now provides circuit bypassing concurrently for both a DC battery 52, and an AC-to-DC converter 50. Power disable/conditioning circuit 58 also provides additional disable circuitry illustrated in FIG. 3.

A dual primary, transformer/rectifier circuit 62 has two primary windings instead of the single primary used in circuit 32 of FIG. 1. The first primary winding is connected to the VDC output from power disable/- conditioning circuit 58. The second primary winding is connected to the Vbattery output from power disable/conditioning circuit 58. The secondary winding of the transformer is connected to an optocoupled capacitor current sense circuit 64, safety circuit 30, a differential amplified capacitor voltage metering circuit 66, and an energy storage capacitor 68. Transformer 62 provides an isolation barrier between the power supply circuitry coupled to the primary winding and the charge capacitor and monitoring circuitry coupled to the secondary winding. This isolation barrier protects the patient and operator from high voltages on the secondary winding of transformer 62 and from the energy stored on energy storage capacitor 68.

A low current switch in low current switch/switch driver circuit 60 is coupled to a low current primary winding on dual primary transformer/rectifier circuit 62. A driver circuit in low current switch/switch driver circuit 60 drives both the low current switch and high current switch 34. High current switch 34 is coupled to a high current primary winding on dual primary transformer/rectifier circuit 62. FIG. 3 provides a more detailed diagram of dual primary transformer/rectifier circuit 62, low current switch/switch driver circuit 60, high current switch 34, primary current sense 36, and the disable circuitry of power disable/conditioning circuit 58.

Optocoupled capacitor current sense 64 performs substantially the same function as capacitor current sense 38 in FIG. 1. Changes to the circuits involve optocoupling between the input and output. The circuit is shown in detail in FIG. 6.

Differential amplifier capacitor voltage metering circuit 66 performs substantially the same function as capacitor voltage metering circuit 40 in FIG. 1. The output, however, is now the scaled voltage difference across the secondary of the dual primary transformer. This circuit is shown in detail in FIG. 7.

A low voltage sense circuit 56 is similar to low battery sense 26 in FIG. 1 except low voltage sense circuit 56 now receives an additional defibrillator control signal, AC ON charger (ACONCH). The ACONCH signal goes high when the DC supply voltage VDC is connected to the defibrillator charging circuit and goes low when VDC is disconnected. Low voltage sense 56 is illustrated in detail in FIG. 8.

FIG. 3 is a detailed circuit diagram of low current switch circuit 60A and switch driver circuit 60B, the disable circuitry of power disable conditioning circuit 58, high current switch 34, primary current sense 36, and dual primary transformer/rectifier circuit 62 in FIG. 1.

Dashed box 60B identifies the switch driver circuit in low current switch/switch driver circuit 60 and dashed box 60A identifies the low current switch of low current switch/switch drive circuit 60 (FIG. 2). Dashed box 36 surrounds the primary current sense in FIG. 2 and dashed box 34 surrounds the high current switch in FIG. 2. The disable circuitry of the power disable/conditioning circuit of FIG. 2 is surrounded by dashed box 58 and the dual primary transformer/rectifier circuit of FIG. 2 is surrounded by dashed box 62.

Input terminal 74 of circuit 60B is coupled to the output of PWM 28 (FIG. 2) and to the first terminals of resistors 78 and 76. The second terminal of resistor 78 is coupled to output terminal 80 and to ground by resistor 82. The second terminal of resistor 76 is connected to the anode of diode 84 and to the base of transistor 86.

The cathode of diode 84 is connected to the emitter of transistor 86, the cathode of Zener diode 88, and to the first terminals of resistors 90 and 92 in high current switch 34 and resistor 106 in circuit 60A. The collector of transistor 86 and the anode of Zener diode 88 are connected to ground.

In high current switch 34, the second terminal of resistor 90 is coupled to the gate of field effect transistor (FET) 102 and the second terminal of resistor 92 is coupled to the gate of FET 104. The source of FET 102 is connected to the source of FET 104, and to the first terminal of resistor 94 and the first terminal of resistor 96 in current sense circuit 36. The second terminal of resistor 96 is connected to output terminal 100 and the first terminal of capacitor 98. The second terminal of resistor 94 and the second terminal of capacitor 98 are coupled to ground.

The drain of transistor 102 is coupled to the drain of transistor 104, the cathode of Zener diode 106 and the dotted terminal of the high current primary winding 144 of transformer 126 in circuit 62. The anode of Zener diode 106 is coupled to ground. The gate of FET 110 is coupled to the second terminal of resistor 106 and the source of FET 110 is coupled to ground. Zener diode 108 is coupled at the anode to ground and coupled at the cathode to the drain of transistor 110 and to the dotted terminal of a low current primary winding 142 of transformer 126.

Power disable/conditioning circuit 58 (FIG. 2) has an input terminal 112 which receives supply voltage VDC (conditioned AC-to-DC converter output) and an input terminal 118 which receives the battery output voltage Vbattery (conditioned battery output). The supply voltage is coupled through a diode 114 to the non-dotted terminal of the low current primary winding 142 of transformer 126. A capacitor 116 connected to the cathode of diode 114 is coupled to ground to filter VDC. The battery voltage input at terminal 118 is coupled through fuse 120 to the non-dotted terminal of the high current primary winding 144 of transformer 126. Capacitor 122 and 124 capacitively couple Vbattery to ground.

The secondary winding 148 of transformer 126 has a diode 128 connected at its dotted terminal and a diode 132 connected at its non-dotted terminal so as to conduct current unidirectionally from terminal 72 toward terminal 70. Zener diode 130 is coupled between diode 128 and terminal 70 and blocks current until its reverse bias avalanche voltage is exceeded at the anode.

Dual Primary Transformer

Figure 4:
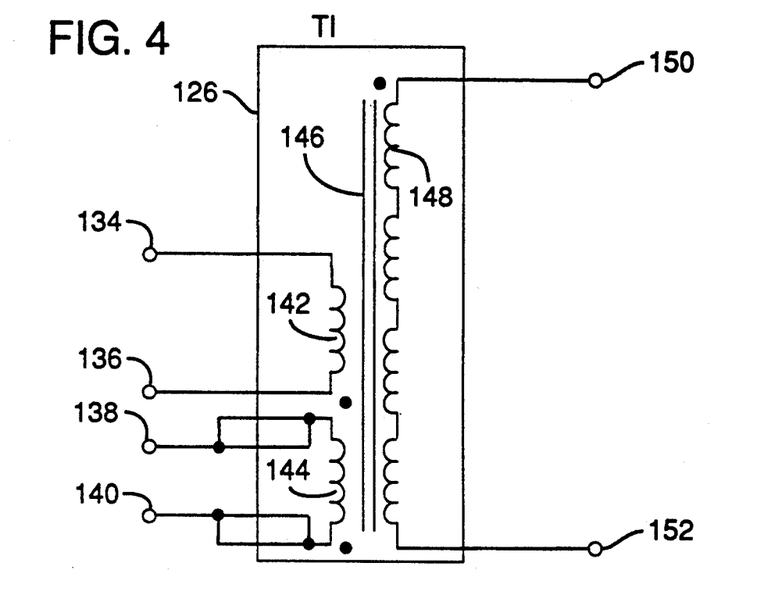
FIG. 4 is a detailed circuit diagram of the transformer in FIG. 3.

FIG. 4 is a detailed schematic of transformer 126 in FIG. 3. Low current primary winding 142 is coupled at the dotted terminal to the drain of FET 110 and coupled at the non-dotted terminal to the cathode of diode 114. High current primary winding 144 is coupled at the dotted terminal to the drain of FETs 102 and 104, and is coupled at the non-dotted terminal to Vbattery. The secondary winding of the transformer is coupled at the dotted terminal to the anode of diode 128 and is connected at the non-dotted terminal to the cathode of diode 132.

The turns for each winding on transformer 126 are listed in Table. 1.

TABLE 1

| Winding | Number of turns |
|---------|-----------------|
| 142 | 11 |

TABLE 1-continued

| Winding | Number of turns |
|---|---|
| 144 | 6 |
| 148 | 534 |

The turn ratios for the transform are as follows:
Primary winding 144 to secondary winding = 1:89
Primary winding 142 to secondary winding = 1:48
Primary winding 144 to primary winding 142 = 1:1.8.
The number of turns and the associated parametric data selected for the primary windings 142 and 144 of the transformer 126 are selected to match the output characteristics of the power supplies VDC and Vbattery, respectively. Matching the output characteristics of each power supply with the input characteristics of the associated primary winding optimize the peak power each power supply can deliver to the transformer 126.

Figure 5:
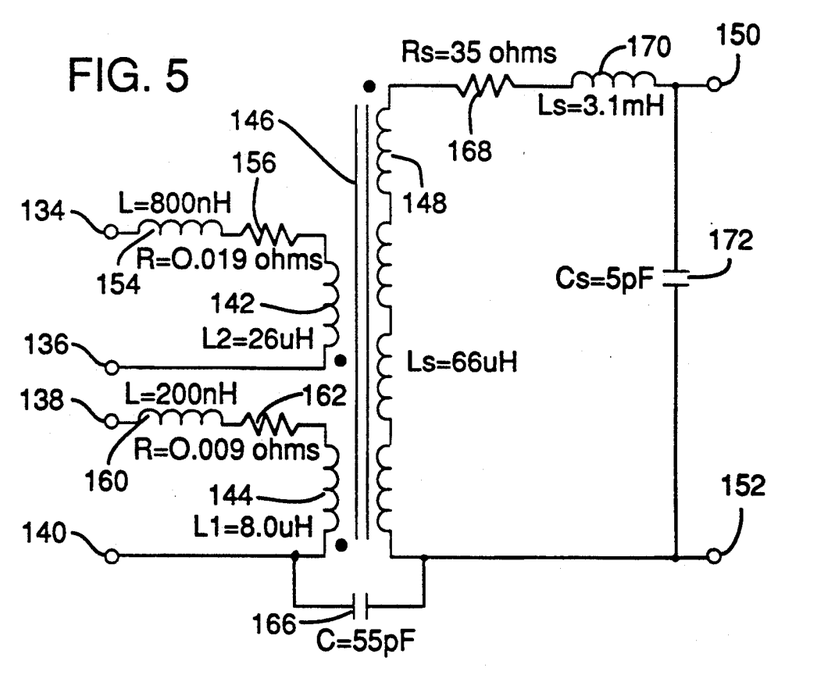
FIG. 5 is a parametric representation of the transformer in FIG. 3.

FIG. 5 is a parametric representation of transformer 126. Primary winding 144 has an input impedance of 0.009 ohms, a leakage inductance of 200 nH, and a primary winding inductance of 8.0 uH. Primary winding 142 has a input impedance of 0.019 ohms, leakage inductance of 800 nH, and a primary winding inductance of 26 uH. The secondary winding has a 35 ohm input impedance, a 3.1 mH leakage inductance, and a 66 uH secondary winding inductance. A capacitance of 55 pF exists between the primary and secondary windings and a 5 pF capacitance exists across the second winding. The breakdown voltage of the transformer is 8 thousand volts.

Referring back to FIG. 3, transformer 126 operates in a fly-back mode with diode 128 acting as a flywheel. The current from Vbattery is allowed to pass to the high current winding of transformer 126 when FETs 102 and 104 (A1) turn on. The current from VDC is allowed to pass to the low current primary winding of transformer 126 when FET 110 (Q12) is turned on. Thus, FETs 102, 104, and 110 create an alternating field across the primary windings of the transformer 126 by intermittently being turned on and off. A voltage across either primary winding produces a negative voltage at the anode of diode 128. The voltage is approximately equal in magnitude to the voltage applied to the primary windings times the turns ratio between the energized primary winding and the secondary winding. During this phase, only the primary windings are active and the transformer is treated as a series inductor. Thus, the primary inductance causes the current in the primary winding to increase linearly according to the relationship;

$$\Delta I = (V_i \times \Delta T)/L_p$$

where
$V_i$ = the voltage across the primary windings
$\Delta T$ = amount of time voltage is applied across the primary winding
$L_p$ = the inductance of the primary winding.
While diode 128 is reverse biased, energy stored in the transformer is equal to:

$$E_t = (\tfrac{1}{2})(L_p \times I_p)$$

where $I_p$ = the total current passing through the primary winding.

When the high current switch (FETs 102 and 104) and low current switch (FET 110) turn off, the flux in the core 146 of transformer 126 causes current to flow in the secondary winding. The secondary voltage rises rapidly, forward biasing rectifier 128 and reverse biasing Zener diode 130 sufficiently to operate in the reverse voltage avalanche region. This allows current from transformer 126 to pass into storage capacitor 68 (FIG. 2). The initial current passing through diode 128 is related to the ending primary current supplied at the transformer primary, times the primary to secondary turns ratio. Since the secondary winding inductance is held at a nearly constant voltage, which is approximately equal to the storage capacitor voltage, the current ramps down nearly linearly with time.

Transformer discharge time becomes shorter as the storage capacitor voltage increases. Therefore, the delay time between each charging cycle is adjusted accordingly. For example, initially no energy resides within storage capacitor 152 and a maximum amount of time is required to discharge energy from the transformer into the storage capacitor. As the energy in the storage capacitor increases, the time required to discharge the energy from the transformer is reduced. Since capacitor current sense circuit 64 (FIG. 2) re-enables the modulator as soon as the transformer discharging cycle is completed, the deactivation time of the modulator between charging cycles is reduced as more energy is stored in the storage capacitor. Therefore, the overall charge time required for charging the storage capacitor is minimized.

A high input signal from PWM 28 at terminal 74 in FIG. 3 forward biases diode 84, causing FET 110 (Q12) FETs 102, 104 (A1) to turn on. Depending on the status of Vbattery and VDC, Q12 passes current from the low current primary winding 142 of transformer 126 and A1 passes current from the high current primary winding 144 of transformer 126. Initially, there is no voltage drop across A1. Therefore, the high current primary winding 144 has the entire voltage output of Vbattery.

Vbattery is stepped up and reflected across the low current primary winding 142 in proportion to the primary-to-primary turn ratio. For example, with 11 turns on the low current primary winding 142 and 6 turns on the high current primary winding 144, the stepped-up voltage across the low current winding is:

low current primary winding
voltage = 1.8 × Vbattery.

Capacitor 116 in conditioning circuit 58 is charged to the stepped-up value of Vbattery. Therefore, if the value of VDC is 14.0 volts and the voltage output of Vbattery is 9 volts, the voltage across the low current primary winding is approximately 16.2 volts. This reverse biases diode 114, preventing battery current from flowing into the AC-to-DC converter. As the on time of A1 continues, the current increases, storing more energy in transformer 126. Also, as current increases through A1, the voltage across the high current winding decreases, allowing capacitor 116 to discharge some of its stored energy through the low current winding into transformer 126.

When the charge rate ramp generator 22 (FIG. 2) reaches the voltage of charge rate threshold generator 24 (FIG. 2), the output of PWM 28 goes into a high impedance state, shutting off FET switches A1 and Q12. The energy stored in transformer 126 is thereby transferred to storage capacitor 152 as described above. If the voltage level of the battery is lower than the voltage at the low current winding 142 generated by Vbattery, diode 114 becomes forward biased, allowing VDC to contribute to the charging of the transformer. The added contribution of energy from VDC allows the storage capacitor to be charged within necessary time limits. The amount of current supplied by Vbattery and VDC is then dependant upon their present output voltage values.

If the battery output voltage is extremely low, VDC produces a voltage at the high current primary winding 144 greater than Vbattery. In this state, VDC dumps current into the battery, charging it. This is a fault condition that requires more time than normally required to charge the storage capacitor.

Therefore, the dual primary windings allow either power supply, or both, to supply energy to the transformer without having to physically disconnect one power supply before connecting the second power supply. The dual primary windings also isolate faults occurring on either power supply.

Resistors 94 and 96, and capacitor 98 comprise primary current sense 36 in FIG. 1. The voltage across resistor 94 indicates the amount of current flowing in the primary side circuit. The voltage at output terminal 100 is coupled to the non-inverting sense input of PWM 28, and is compared with a reference voltage. If the voltage across resistor 94 is greater than the preset reference voltage, PWM 28 is disabled, shutting off A1 and Q12. Resistor 96 and capacitor 98 filter out spurious ringing due to primary/secondary parasitic signals in transformer 126.

Diode 84 and PNP transistor 86 (Q9) serve as an active pull down circuit for FET switches A1 and Q12. To disable switches A1 and Q12, the output of PWM 28 is placed in a high impedance state. Pull down resistors 78, 82, and 76 thereby draw current from the base of transistor Q9 while diode 84 restricts current flow between the FETs and the base of transistor Q9. The negative base current turns on Q9, pulling down the gate-to-source voltage on FET switches A1 and Q12. Switches A1 and Q12 thereby shut off, disabling the power supplies. Switches A1 and Q12 are turned on when PWM 28 generates a high output voltage at input terminal 74. The positive voltage at terminal 74 turns off Q9 and forward biases diode 84. As transistor Q9 shuts off, the gate-to-source voltages of FET switches A1 and Q12 increase. In turn, switches A1 and Q12 turn on, enabling the power supplies.

The low impedance path to ground created by Q9, quickly discharges the internal capacitance in both switches A1 and Q12. Therefore, switches A1 and Q12 quickly turn off, minimizing energy loss. Resistors 78 and 82 scale the output voltage of PWM 28 at terminal 80, which is supplied to capacitor current sense 64 (FIG. 2).

Several components and physical design features have been put in the charger circuit to increase system reliability. For example, diode 128 is mounted on a printed circuit board with large copper pads at each mounting hole to act as heat sinks. A slot is cut out underneath the diode to provide a larger creep path for better cooling. Zener diodes 88, 106, and 108 provide high voltage transient suppression, protecting FET switches A1 and Q12 from exceeding maximum drain-to-source voltage ratings. For example, the maximum working voltage for switch A1 is 72.4 volts; therefore, the breakdown voltage for Zener diode 106 is set for 82 volts nominal.

A heat sink has been attached to switch A1 to reduce overheating. The following heat sink calculations were used to provide the necessary thermal resistance:

$$R_{\theta sa} = [(T_J - T_A)/P_D] - R_{\theta jc} - R_{\theta cs} \quad (1)$$

where
$T_J$ = junction temperature of the transistor = 150° C.
$T_A$ = ambient temperature = 70° C.
$P_D$ = transistor power dissipation = 8.8 watts
$R_{\theta jc}$ = junction to case thermal resistance = 0.833° C./w
$R_{\theta cs}$ = case to sink thermal resistance = 0.9° C./w
$R_{\theta sa}$ = sink to ambient thermal resistance.

Therefore, the sink-to-ambient thermal resistance is $R_{\theta sa} = 7.4°$ C./w. A Thermalloy, Grafoil 7020 Conducta-Pad heat sink with a thermal resistance of 9.0° C./w is therefore used with both A1 and Q12.

Optocoupled Capacitor Current Sense

Figure 6:
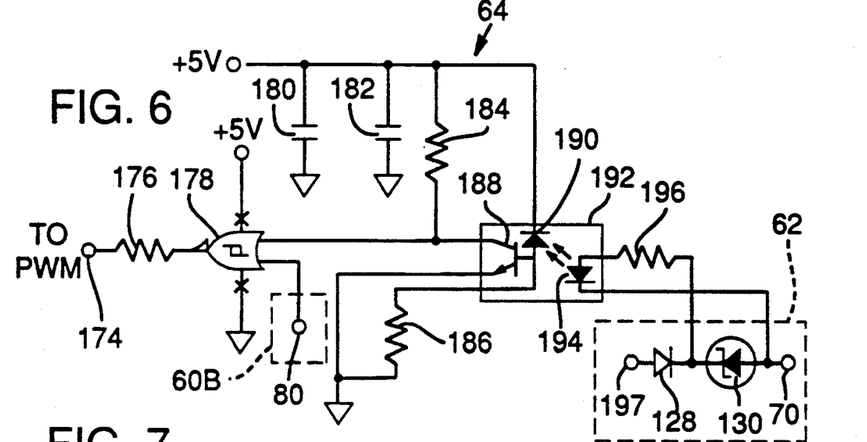
FIG. 6 is a detailed circuit diagram of the optically coupled capacitor current sense circuitry in FIG. 2.

FIG. 6 is a circuit diagram of optocoupled capacitor current sense circuit 64 in FIG. 2. Terminal 70 from circuit 62 (FIG. 3) is coupled to the anode of Zener diode 130 and to the cathode of light emitting diode 194. The cathode of Zener diode 130 is coupled to the cathode of diode 128 from circuit 62 and resistively coupled to the anode of light emitting diode 194 by resistor 196. The anode of diode 128 is coupled at input terminal 197 to the dotted terminal of secondary winding 148 in circuit 62 (FIG. 3). The base of transistor 188 is coupled to the anode of photodiode 190 and resistively coupled to ground by resistor 186. The emitter of transistor 188 is coupled to ground. A reference voltage is connected to the cathode of photodiode 190, and the first terminal of resistor 184. Capacitors 180 and 182 capactively couple the reference voltage to ground. Input terminal 80 from circuit 60B (FIG. 3) is coupled to the first input NOR gate 178. The second input of NOR gate 178 is connected to the collector of transistor 188 and the second terminal of resistor 184. Output terminal 174 is coupled to the oscillator input of PWM 28 and resistively coupled by resistor 176 to the output of NOR gate 178. Transistor 188, photodiode 190, and light emitting diode 194 comprise the internal circuitry of optocoupler 192.

When current begins to flow on the secondary side of transformer 126 (FIG. 2), Zener diode 130 breaks down and Zeners voltage across light emitting diode 194 and resistor 196. Resistor 196 limits the current through the light emitting diode. Zener diode 130, in the Zener breakdown voltage region, causes current to flow through light emitting diode 194, increasing the reverse leakage current in photodiode 190. The increased leakage current causes transistor 188 to turn on, thereby pulling down the voltage at the second input of NOR gate 178. If the scaled PWM output at input terminal 80 is also low (disabled state), the output of NOR gate 178 goes high, disabling PWM 28. This prevents the PWM from initiating another charge cycle until current from the transformer has completely discharged into the storage capacitor.

When current stops flowing on the secondary side of transformer 126, the voltage across Zener diode 130 falls to zero, disabling light emitting diode 194. The disabled light emitting diode 194 decreases the reverse leakage current in photodiode 190, thereby causing transistor 188 to turn off. Resistor 184 pulls the second input of NOR gate 178 high, causing the output of NOR gate 178 to go high, thereby causing PWM 28 to generate a high output. NOR gate 178 has Schmitt triggered inputs to reduce noise effects and to quickly enable the PWM when current no longer flows in the secondary winding of the transformer. Bypass capacitors 180 and 182 filter any noise on the voltage reference that could inadvertently activate NOR gate 178.

Diff-Amp Capacitor Voltage Metering

Figure 7:
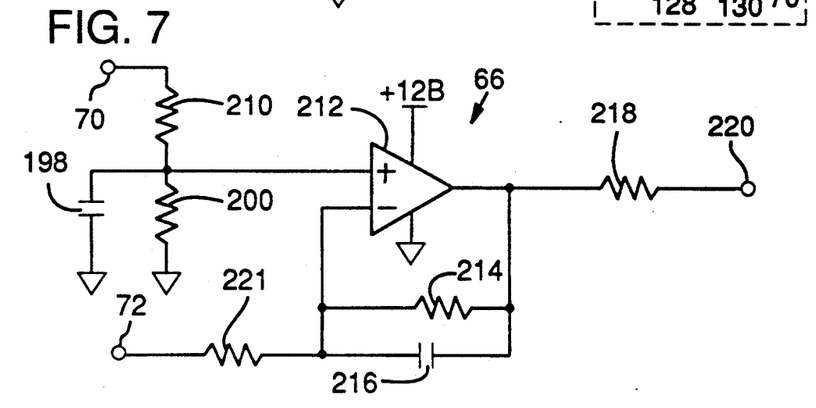
FIG. 7 is a detailed circuit diagram of the differential amplified capacitor voltage metering circuit in FIG. 2.

FIG. 7 is a detailed schematic diagram of the differential amplifier capacitor voltage metering circuit 66 of FIG. 2. Input terminals 70 and 72 are coupled across opposite ends of storage capacitor 68 (FIG. 2). The non-inverting input of op-amp 212 is resistively coupled to terminal 70 by resistor 210, resistively and capacitively connected to ground by resistor 200 and capacitor 198. The inverting input of op-amp 212 is resistively coupled to input terminal 72 by resistor 221. The output of op-amp 212 feeds back into its inverting input through resistor 214 and capacitor 216 and is resistively coupled to output terminal 220 by resistor 218. Output terminal 220 is coupled to the inverting input of PWM 28.

The capacitor voltage metering circuit scales the difference between the voltage levels on either side of the energy storage capacitor. The scaled value output by op-amp 212 is determined by the values of resistors 210, 200, 221, and 214. For example, resistor 200 and resistor 214 are chosen to be the same value ($R_1$) and resistor 210 and resistor 221 are chosen to be the same value ($R_2$). The output voltage of op-amp 212 is then:

$$V_{out} = (R_2/R_1) \times (V_{70} - V_{72})$$

where $V_{70}$ = the voltage at input terminal 70.
$V_{72}$ = the voltage at input terminal 72.

Selecting values for resistors 200 and 214 ($R_1$) significantly greater than the value for resistors 210 and 221 ($R_2$), generates a scaled value of the capacitor voltage at the output of the op-amp.

The output from op-amp 212 is compared to a reference voltage set in PWM 28. If the op-amp output exceeds the reference voltage, the output of PWM 28 is disabled, preventing any additional charging cycles in the defibrillator charging circuit.

The scaled voltage output signal is also sent to the defibrillator control board. The control board monitors the storage capacitor voltage, maintaining enable signals to the modulator if the storage capacitor has not obtained the required voltage. When the storage capacitor has reached the desired charge level, the defibrillator control circuit sends disable signals to charge enable circuit 20 and charge rate threshold generator 24 (FIG. 2). Capacitor 198 filters noise from the non-inverting input of op-amp 212. Feedback capacitor 216 increases the stability of the voltage measuring circuit by reducing oscillation effects at the output of op-amp 212.

Low Input Voltage Sense

Figure 8:
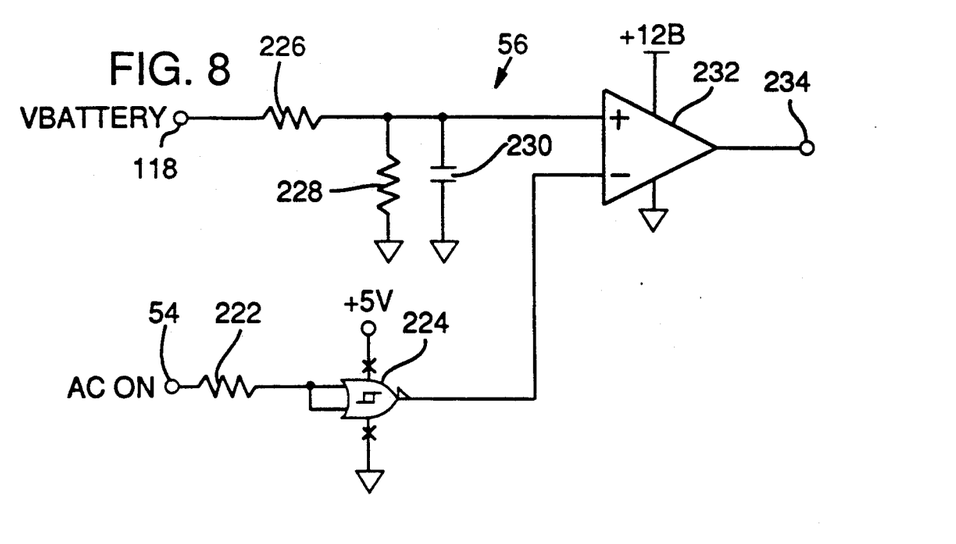
FIG. 8 is a detailed schematic diagram of the low voltage sense circuit in FIG. 2.

FIG. 8 is a detailed schematic diagram of low input voltage sense circuit 56 in FIG. 2. Input signal Vbattery at terminal 118 is connected through resistors 226 to the non-inverting input of op-amp 232. Resistor 228 and capacitor 230 couple the noninverting op amp input to ground. Input terminal 54 receives an AC ON charger signal from the defibrillator control board. The AC ON signal passes through resistor 222 to both the first and second inputs of NOR gate 224. The output of NOR gate 224 feeds the inverting input of op-amp 232. The output of op-amp 232 is coupled to the inverting comparator input of PWM 28.

Resistor 226 and resistor 228 divide the Vbattery voltage at the non-inverting input of op-amp 232. If VDC is connected to the defibrillator circuit, the AC ON signal at input terminal 54 is high, causing the output of NOR gate 224 to go low. This causes any positive Vbattery voltage to drive the output of op-ap 232 into a high impedance state, keeping the output of PWM 28 high. If VDC is disconnected from the defibrillator circuit, however, the voltage at input terminal 54 is low, causing the voltage at the inverting input of op-amp 232 to go high. Therefore, if the scaled battery voltage level at the non-inverting input of op-amp 232 falls below the output voltage of NOR gate 224, the output of op-amp 232 goes low, disabling PWM 28. PWM 28 remains disabled until the battery voltage increases sufficiently to disable the low output from op-amp 232.

The output of op-amp 232 goes low when a battery voltage output is too low to maintain both normal defibrillator operations and charging operations. For example, upon initiation of a charging cycle, current is drawn from the battery reducing its output voltage. If the battery voltage is initially too low, the additional current drain from the charging circuit draws the output voltage of the battery to low to maintain normal defibrillator operation. This condition is only critical when the AC power supply is not attached (e.g., the voltage at input terminal 54 is low), since the defibrillator system is powered by VDC when it is attached to the charging circuit. Disabling the charging circuit during this condition also protects the battery from damage due to excessive current drain.

Having described and illustrated the principles of the invention in a preferred embodiment thereof, it should be apparent that the invention can be modified in arrangement and detail without departing from such principles.

We claim all modifications and variation coming within the spirit and scope of the following claims:

1. A cardiac defibrillator charging circuit for charging an energy storage capacitor from multiple power supplies comprising:
   a battery having an energy output,
   a DC voltage supply having an energy output,
   a high voltage storage and discharge capacitor,
   a transformer having a first primary winding, a second primary winding, and a secondary winding, the secondary winding coupled across the capacitor; and
   switching circuitry for intermittently connecting the battery to the first primary winding and for intermittently connecting the DC voltage supply to the second primary winding creating alternating fields across the first and second primary windings.

2. A cardiac defibrillator according to claim 1 wherein the battery and the DC voltage supply each have a given output characteristic and the first and second primary windings of the transformer each have input characteristics that substantially match the output characteristics of the battery and DC voltage supply, respectively.

3. A cardiac defibrillator according to claim 2 in which the transformer has a turns ratio between each primary winding and the secondary winding that maximizes energy transfer from the respective primary winding to the secondary winding.

4. A cardiac defibrillator according to claim 1 in which the first and second primary windings allow the DC voltage supply and the battery to charge the energy storage capacitor at different rates.

5. A cardiac defibrillator according to claim 1 in which the first and second primary windings are electrically isolated thereby electromagnetically isolating faults in the battery and DC voltage supply.

6. A cardiac defibrillator according to claim 1 in which the switching circuitry intermittently couples one of said battery and said power voltage supply to one of said first and second primary windings respectively.

7. A cardiac defibrillator as in claim 1 in which the switching circuitry and the first and second primary winding allow the energy output from the battery or the DC voltage supply to be applied to one of said primary windings.

8. A cardiac defibrillator as in claim 1 in which the switching circuitry allows the DC power supply to discharge energy to the battery when the DC power supply generates a voltage at the first primary winding greater than the battery voltage.

9. A quick charging cardiac defibrillator comprising:
a battery,
a DC voltage supply,
a high voltage storage and discharge capacitor,
a transformer having first and second primary windings and a secondary winding,
switching means for intermittently connecting the battery and DC voltage supply to the first and second primary windings of the transformer respectively creating alternating fields across the first and second primary windings; and
means for coupling the secondary winding of the transformer to the high voltage storage and discharge capacitor.

10. A cardiac defibrillator as in claim 9 including means for uncoupling the secondary winding from the high voltage storage and discharge capacitor when the switching means connects one of said battery and DC voltage supply to said first and second primary windings respectively.

11. A cardiac defibrillator as in claim 10 including means for changing the frequency at which the switching means enable the discharge of energy from the battery and the DC voltage supply to the first and second primary windings respectively.

12. A cardiac defibrillator as in claim 11 in which the frequency changing means is responsive to the dispersion of energy to the energy storage capacitor from the secondary winding of the transformer.

13. A cardiac defibrillator as in claim 9 including means for coupling the secondary winding to the capacitor when energy is discharged from the transformer into the capacitor and decoupling the secondary winding from the capacitor when the discharge of energy into the capacitor is complete.

14. A method for charging a high voltage storage and discharge capacitor in a cardiac defibrillator, the method comprising:
providing a first DC power supply and a second DC power supply each having given output characteristics;
providing a transformer having first and second primary windings with given input characteristics and a secondary winding;
coupling the secondary winding across the high voltage storage and discharge capacitor,
intermittently coupling and decoupling the first DC power supply and the second DC power supply respectively to the first and second primary windings of the transformer,
transforming the energy from at least one of the first and second power supplies into a single high voltage output; and
discharging the transformed energy into the high voltage storage and discharge capacitor.

15. The method of claim 14 further comprising the step of matching the output characteristics of the first and second power supplies with the input characteristics of the first and second primary winding of the transformer respectively.

16. The method of claim 14 further comprising the step of isolating faults on the first primary winding, the second primary windings, and the secondary winding by separately coupling each winding electromagnetically to the transformer.

17. A method of claim 14 further comprising the step of uncoupling the first and second power supplies from the first and second primary windings when the transformer is discharging energy into the high voltage storage and discharge capacitor.

18. A method of claim 14 further comprising the step of charging the transformer at the same time through the first primary winding with the first DC power supply and through the second primary winding with the second DC power supply.

19. A method of claim 14 further comprising the step of charging the transformer selectively by one of the first and second power supplies when the output of the non-selected DC power supply is below a preset voltage.

20. A method of claim 14 in which the first DC supply is a battery, the second DC power supply is an AC-to-DC converter and further comprising the step of charging the battery from the AC-to-DC converter when the battery output is below a predetermined output voltage.

* * * * *